US006863846B1

(12) United States Patent
Zubkova et al.

(10) Patent No.: US 6,863,846 B1
(45) Date of Patent: Mar. 8, 2005

(54) COMBUSTION RETARDANT FOR POLYMERIC MATERIALS

(75) Inventors: Nina Sergeevna Zubkova, Moscow (RU); Nataliya Grigorievna Butylkina, Moscow (RU); Nikolai Alexandrovich Khalturinsky, Moscow (RU); Alexandr Alexandrovich Berlin, Moscow (RU)

(73) Assignee: Isle Firestop Limited (GB)

(*) Notice: Subject to any disclaimer, the term of this patent is extended or adjusted under 35 U.S.C. 154(b) by 0 days.

(21) Appl. No.: 09/786,719

(22) PCT Filed: Aug. 2, 1999

(86) PCT No.: PCT/RU99/00273

§ 371 (c)(1),
(2), (4) Date: Jun. 22, 2001

(87) PCT Pub. No.: WO00/14094

PCT Pub. Date: Mar. 16, 2000

(30) Foreign Application Priority Data

Sep. 8, 1998 (WO) .............................. PCT/RU98/00289

(51) Int. Cl.[7] .................. C09K 21/10; C09K 21/12; C09K 21/14; C08K 5/5399; C07F 9/44
(52) U.S. Cl. ................... 252/609; 524/133; 524/136; 564/12
(58) Field of Search ..................... 252/609; 524/133, 524/136; 564/12

(56) References Cited

U.S. PATENT DOCUMENTS

| 4,308,197 A | 12/1981 | Byrd et al. |
| 4,918,122 A | 4/1990 | Dellar et al. |

FOREIGN PATENT DOCUMENTS

| EP | 0254683 | 1/1988 |
| EP | 0533102 | 3/1993 |
| EP | 1113018 | 7/2001 |
| GB | 1526361 | 9/1978 |
| GB | 2259707 | 3/1993 |
| RU | 2099367 | 3/1993 |
| RU | 2024560 | 12/1994 |
| RU | 2099384 | 12/1997 |
| RU | 2103314 | 1/1998 |
| WO | WO87/00187 | 1/1987 |

OTHER PUBLICATIONS

HCAPLUS 1987:68418, Document No. 106 :86418, "Inhibition Of The Combusion Of Cellulose By Phosphorus–Containing Compounds" Sultanov et al.,Koksnes Kimija (6), 44–6 (Russian) 1986, CODEN: KHDRDQ. ISSN: 0201–7474.*

"L–Polynosic Fibres," Encyclopaedia of Polymers, 1974, vol. 2, pp 247–248.

Zubova, N.S., M.A. Tyuganova, I.S. Reshetnikov, and N.A. Khalturinskii, "Decreasing The Combustability of Polyolefins Using Microencapsulated Fire Retardants," Fibre Chemistry, 1997, vol. 29, No. 3.

* cited by examiner

*Primary Examiner*—Joseph D. Anthony
(74) *Attorney, Agent, or Firm*—Garvey, Smith, Nehrbass & Doody, L.L.C.; Seth M. Nehrbass; Brett A. North

(57) ABSTRACT

A description is given of a combustion retardant for polymer materials in the form of a new complex compound of the ammonium salt of amide of alkylphosphonic acid with ammonium chloride, and also of processes for producing various polymer materials using the said combustion retardant.

35 Claims, No Drawings

COMBUSTION RETARDANT FOR POLYMERIC MATERIALS

TECHNOLOGY FIELD

The invention relates to a technology for producing polymer compositions based on carbon-chain polymers (polyethylene, polypropylene, polystyrene, synthetic rubbers and copolymers of various compositions), heterochain polymers (polyester, epoxy and phenol resins) and composition materials of various compositions and fillings with low combustibility, low toxicity of gases emitted during combustion and low smoke emission.

Polymer materials are widely used in the cable and motor industries, electrical consumer goods, construction, other consumer goods, the gas and oil extraction industries, aviation and space technology and for making packing materials.

PRIOR ART

A significant problem with the majority of industrially produced polymer materials is their high flammability and high rate of combustion, accompanied by the emission of a large quantity of toxic products.

With the aim of reducing the combustibility of carbon-chain polymers, physical (Kistelman V. I. Physical Methods of Modifying Polymer Materials, Moscow, Khimiya, 1980, 223 pp.) and chemical methods of modification are used, and also a combination of them, e.g. photochemical modification (Kachan A. A., Zarnotayev P. V. The Photochemical Modification of Polyolefins, Kiev, Naukova dumka, 1990, 276 p.). Chemical modification by means of halogenation brings about greater degree of reduction in their combustibility. However, to use this method to obtain a polyolefin which is extinguished when the external heat source is removed, it is necessary to chlorinate polyethylene (PE) and polypropylene (PP) to a halogen content of 2540 wt. % (Aseyeva R. M., Zaikov G. Ye. The Combustion of Polymer Materials, Moscow, Nauka, 1991, 150 pp.). With such a chlorine content, the crystallinity of PE and PP is sharply reduced, so that they are transformed from thermoplastic into elastomers (Sirota A. G. Modification of the Structure and Properties of Polyolefins, Moscow, Khimiya, 1984, 150 pp.). Chlorinated PE finds application as a low combustibility material in its own right and as a combustion retardant (CR) of a polymer nature for other polymer materials. The main problems with chlorinated polyolefins are their low thermal stability and their emission of toxic products, which limit their application.

Polymers with higher thermal stability and oxygen index (OI) (above 27%) can be obtained by sulfochlorination (Aseyeva R. M., Zaikov G. Ye. The Combustion of Polymer Materials, Moscow, Nauka, 1991, 150 pp.). Like chlorination, sulfo-chlorination can lead to the formation of elastomers.

(N. B. OI, the oxygen index, is the minimum content of oxygen in a mixture with nitrogen at which stable combustion of a specimen is observed.)

For the chemical modification of polystyrene, styrene is copolymerised with monomers containing chlorine, bromine or phosphorus: vinyl chloride, vinyl bromide, vinylidene chloride, chlorinated and bromated styrenes, acrylates containing halogens, halogenated fumarates, N-phenylmaleimides, phosphorylised styrene, halogenated esters of vinyl- and allylphosphonic acids, phenyldichlorophosphine and tris(methacryloilbromethyl) phosphate (Low Combustibility Polymer Materials, ed. A. N. Pravednikov, Moscow, Khimiya, 1986, 132 pp.).

The method of chemical modification of carbon-chain polymers with the aim of imparting fireproofing properties to them enables a fireproofing effect which is resistant to various treatments to be obtained. However, it requires changes in the technology for producing the polymer, and leads to the appearance of a number of negative properties in the end product, which limits the application possibilities for this method.

In scale of use, chemical modification methods lag far behind the method of introducing CRs and systems of them at the processing stage of the polymers (Berlin A. A., Volfson S. A., Oshmyan V. G. et al. Principles of the Creation of Fireproofed Polymer Materials, Moscow, Khimiya, 1990, 240 pp.)

The process of producing low combustibility synthetic materials by the introduction of CRs into the polymer melt during moulding makes it possible to retain the existing technology for processing articles, is highly economical and creates conditions for developing ecologically clean processes. It also ensures that the fireproofing is highly resistant to wet treatments.

As CRs for rubbers, the most widely used are aluminium trihydroxide and aluminium oxide, which not only reduce the combustibility of the rubber, but also eliminate the disadvantage of smoke emission.

However, to produce compositions which do not support combustion in air, the degree of filling of the polymer composition with combustion retardant must be not less than 50%, which complicates the process of treating the compositions and reduces the physical and mechanical indicators (Low Combustibility Polymer Materials, ed. A. N. Pravednikov, Moscow, Khimiya, 1986, 132 pp.).

There are known joint uses of $Al(OH)_3$ and $Mg(OH)_2$ in combination with swelling graphite (Khokhlova L. A., Aseyeva R. P., Ruban L. V., International Conference on Low Combustibility Polymer Materials. Alma-Ata, 1990, Vol. 1, pp. 16–18).

A big problem in processing inert CRs is the migration of additives (not compatible with the polymer lattice) from the polymer lattice to its surface, since these additives are not bonded to it. This leads to a reduction in the fire retardant effect, and in contact with the surface of metals, increases corrosion activity with the surface of the metals.

More effective CRs for polyolefins and synthetic rubbers are bromoorganic ones which are introduced into polymers in combination with a synergic additive —antimony trioxide (U.S. Pat. No. 5,116,898, MPC C 08K 5/06). The replacement of part of the trioxide enables the CR content to be reduced. To reduce the combustibility of polystyrene, halogenated aliphatic compounds are used in combination with antimony trioxide: chloroparaffins, perchlorinated alkanes $C_2Cl_6$-$C_4C_{10}$, aliphatic compounds containing bromine (tetrabromethane, tetrabromoctane, 1,2,3,4-tetrabromine 2,3-dimethylbutane, 2,3,4,5-tetrabromine-2,5-dimethylhexane and others (Low Combustibility Polymer Materials, ed. A. N. Pravednikov, Moscow, Khimiya, 1986, 132 pp.).

To impart self-extinguishing properties to polyolefins and synthetic rubbers, organic CRs must be used in high concentrations (up to 40% chlorine or 20–30% bromime).

Several publications describe the use of red phosphorus (the polymer form of elemental phosphorus) as a CR for polyolefins (Low Combustibility Polymer Materials, ed. A.

N. Pravednikov, Moscow, Khimiya, 1986, 132 pp.). A polyethylene with OI 26.2% has an 8% content of phosphorus. However, in processing polyolefins containing red phosphorus, toxic phosphorous hydrogen (phosphine) is emitted.

There is a known use of ammonium polyphosphates as CRs for polyolefins and synthetic rubbers (Application 2272444 Great Britain, MPC C 08F 8/40, C08F 9/44).

The effectiveness of the action of ammonium polyphosphates depends on how finely they are crushed. However, even at a fine degree of dispersion, a high degree of filling (40–50 wt. %) is required to achieve OI 28%, which leads to a considerable reduction in the physical and mechanical properties of the material.

Many studies have been devoted to the synthesis of amides or alkylamides of phosphoric or alkylphosphonic acid and their use as CRs to impart fireproofing properties to polymer materials. The studies carried out by Drews (Drews M. J., Textilveredlung, 1973, Vol. 8, pp. 180–186) showed that compounds containing a P—N bond are more effective CRs than compounds with P—O bonds. The synthesis of phosphorus triamide has been described (Herlinger H. Textilveredlung, 1977, Vol. 12, pp. 13–20) and it is proposed that it should be used to impart fireproofing properties to cellulose materials. The reaction was conducted by the interaction of trichloroanhydride of phosphoric acid with ammonia in chloroform at temperature 10° C. A problem with the CR thus obtained is a reduction of the physical and mechanical indicators of polymer materials modified by this CR by 50–60%.

With the aim of eliminating this problem, pentamethylphosphorotriamide was synthesised by treating phosphorus oxychloride with dimethylamine and methylamine (L Blanc R. B., Text. Chem. Colorist, 1975, Vol. 7, No. 10, pp. 23–25). However, the synthesised compounds possessed high thermal stability, and were therefore less effective as fireproofing for polymer materials.

A method of synthesising diamide of methylphosphonic acid by treating dichloroanhydride of methylphosphonic acid with liquid ammonia in a chloroform medium was proposed in another work (Ratz R. J., Am. Chem. Soc., 1955, Vol. 77, pp. 4170–4171). All the reagents, including the solvent, were dehydrated. However, as was shown in this work, diamide of methylphosphonic acid, which is separated out from the reaction mixture by boiling in a medium of diethylamine and chloroform, has low resistance to the effect of hydrolising agents, and even under the effect of the moisture in the air, diamide of methylphosphonic acid gradually passes through the ammonia salt into the methylphosphonic acid. Due to this problem, this compound cannot be recommended as a CR for introduction into molten polymer.

With the aim of eliminating this fault, RU Patent No. 20993384 proposed the microencapsulation of partly hydrolised diamide of methylphosphonic acid —the ammonium salt of amide of methylphosphonic acid —in a heat-resistant shell based on polyaramides. However, the CR produced has an insufficiently effective fireproofing action for polyolefins, and can be recommended only for a reduction in the combustibility of polyamides and polyesters. It should be noted here that it is difficult to conduct the process of microencapsulation into polyaramide shells without structural defects.

There is a known use of organosilicon compounds to modify CRs and to make it easier to process compositions with high degrees of filling. To make processing easier, modifying additives are introduced into the compositions: e.g., there is a known low-combustibility composition (Bolikhova V. D., Drobinin A. N. Plastic Masses, Moscow, Z.-S. 1994, pp. 46–51) including the antipyrene $Al(OH)_3$, and as a modifying additive, silanic and polysiloxanic acids.

Organic compounds containing halogens are used to modify heterochain polymers, in particular polyesters. These are mainly aromatic CRs containing bromine. They are used because of their higher thermal stability and lower smoke emission in comparison with aliphatic compounds containing halogens (Namets R. C., Plastics Compounding, 1984, Vol. 7, No. 4, pp. 26–39). To reduce smoke emission, special additives are used when CRs containing halogens are being introduced. The most active of these additives are the oxides of aluminium, zinc and tin (Cusack P. A., Fire and Mater., 1986, Vol. 1, No. 1, pp. 41–46).

The problems with using CR containing halogens are the low resistance of the materials produced to the effect of ultraviolet radiation, their high toxicity and corrosion of the equipment during processing.

The above-listed faults are largely inapplicable to CRs containing phosphorus —Bisphenol-S (Horrocks A. P., Polym. Degrad. Stab., 1996, Vol. 54, pp. 143–154). The commercial firm Albright and Wilson market a cyclic phosphonate called Amgard 1045 (Application 2250291 Great Britain MPC C08K 8/03, 7/04).

The introduction of red phosphorus (1–15 wt. %) and melamicyanurate (4–15 wt. %) into a polyester makes it possible to produce a high-strength material (Application 2250291 Great Britain MPC C08K 8/03, 7104). However, the process of the application of high-fire-risk red phosphorus is quite complex. Also, the polyester compositions produced acquire a certain coloration.

The firm "Hoechst" (Germany) produces fireproofed polyester fibres using a bifunctional compound containing phosphorus as a CR. This compound is marketed as Trevira FR and CS (Baranova T. L., Smirnova T. V., Ayzenshteyn E. M. Fireproofed Polyester Fibres. Information Review, Series Chemical Fibre Industry. Moscow, NIITEKhIM, 1986, 42 pp.). However, the fireproofing characteristics of these fibres are not high enough, and for a phosphorus content of 0.8–1.0%, the OI is 26–27%.

One tendency under intensive development in recent years is the introduction of antipyrene additives to polymer compositions in the form of microcapsules.

Encapsulation methods have been worked out for tetrafluorodibromethane (boiling point 47.5° C.) and tetrachlorodifluoroethane (boiling point 92.8° C.). Gelatine and gum arabic are used for the shell. The Italian firm "Eurand" has organised the industrial production of microencapsulated tetrafluorodibromethane (freon —114 B2) (Aleksandrov L. V., Smirnova T. V., Khalturinskiy N. A., Fireproofed Materials, Moscow, VNIIPI, 1991, 89 pp.).

There are known fireproofing compositions in which the antipyrene is enclosed in a polymer shell, e.g. a composition based on polyolefins, containing as combustion retardant $Al(OH)_3$ microencapsulated in a polyurethane shell (EP A 04114971 B 1, C 08 K 9/08, 1995), or a composition including microencapsulated tris-(2,3-dibromopropyl) phosphate in a shell of polyvinyl alcohol or urea-formaldehyde resin (U.S. Pat. No. 3,660,821, cl. 260–2,5, 1972).

Another problem with the known polymer compositions which have a microencapsulated combustion retardant is their high degree of filling with combustion retardant (up to 60%), as a result of which their physical and mechanical indicators are low.

Yet another major problem with the known compositions is the impossibility of processing them at T>200° C. (i.e., they cannot be moulded), since Al(OH)$_3$ becomes degraded at T>180° C., and the polymer shells of the microencapsulated combustion retardants in the known compositions begin to break down even at 160–190° C., leading to the release of the antipyrene from the shell and its decomposition, thus reducing the fire resistance of the compositions and making them more difficult to process.

There is a known polymer composition based on polyolefins, including red phosphorus microencapsulated in melamine formaldehyde resin (EP A 0250662, MPC C 08 K 9/10, 1986). Melamine formaldehyde resin is somewhat more stable than the antipyrene shell in the other known compositions, but at T>200–220° C., it too begins to decompose, followed by the hydrolysis of the red phosphorus and the formation of highly toxic phosphines. Consequently, this is also a composition which cannot be processed by moulding, since this takes place at temperatures which are too high (250–280° C.).

Substance of the invention

In spite of the large number of proposed processes for reducing the combustibility of polymer materials, the problem of creating combustion retardants for polymer materials and more efficient means of producing low-combustibility polymer compositions remains urgent. This invention is primarily directed towards solving it.

Other problems tackled by the invention are:

reducing smoke-forming capacity during the pyrolysis and combustion of fireproofed polymer compositions;

improving the workability of polymer compositions;

making it possible to implement the developed processes using equipment already installed in production lines for the treatment of polyolefins and synthetic rubbers.

The authors of this invention have previously proposed the use of the microencapsulated antipyrene T-2 as a CR for polyethylene and polypropylene (Zubkova N. S, et al., Plastmassy, 1996, No. 5, pp. 35–36). This is a technical mixture of two individual compounds —the ammonium salt of methylphosphonic acid and ammonium chloride.

The authors later discovered, to their surprise, that a complex compound of the ammonia salt of the amide of methylphosphonic acid with ammonium chloride provides more effective fireproofing than the technical mixture referred to above. In the absence of a theory to explain the reason for this unexpected result, it may be supposed that complex compounds are more active catalysts of the coke-formation processes which are responsible for reducing the combustibility of polymer materials.

Thus, the substance of this invention is primarily the creation of a new combustion retardant for polymer compositions, for which we propose complex compounds of the ammonia salt of the amide of alkylphosphonic acid with ammonium chloride (1)

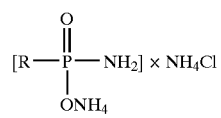

where R is the alkyl radical C—1–3.

It was established experimentally that in the said complex compound, there are about 1.8 molecules of ammonium chloride for one molecule of the ammonium salt of the amide of alkylphosphonic acid.

The new complex compound as in Formula (I) can be produced by the interaction of the dichloroanhydride of alkylphosphonic acid with gaseous ammonia in a medium of organic solvent at a temperature of 10–20° C.

The combustion retardant which is the subject of this invention can be used by various methods.

To impart enhanced fireproofing properties to such polymers as polyethylene, polypropylene and the copolymers of various compositions based on them, the created combustion retardant should be introduced at the polymer processing stage.

Thus, for example, the new combustion retardant can be jointly extruded with the polymer, after which the polymer fibre can be moulded and reprocessed into granules.

Another applied-for process for producing polymer materials of the above type is the mixing of the new combustion retardant with polymer composition and then rolling the mass and pressing it into articles.

For the processes described above, and others, for the production of low fire risk polymer materials, when the combustion retardant developed by the authors is introduced into the polymer in the course of its processing, it is advisable first to microencapsulate the combustion retardant in a polymer shell, capsule size being from, 5 to 25 µm. To produce the microcapsule shell, one may use polyethylene or polyorganosiloxanes, in particular polyvinylmethyldiethoxysiloxane or polyaminopropylethoxysiloxane. To produce low fire risk polymer materials such as polyester and epoxy resins, the new combustion retardant must be introduced into the polymer composition before it sets.

These compositions may find wide application as binders for glass plastics, sealants, cast insulation and adhesives, as protective coatings for various materials and to produce items by casting in many fields of technology, such as the electrotechnical and electronic fields, and also in construction, aviation, shipbuilding etc.

When set, the compositions produced are solid infusible materials which do not dissolve in organic solvents, are resistant to the effect of acids and alkalis, which have good thermal, physical, mechanical and electrical insulation properties, with no volatile components and which are extinguished on being carried out of a flame.

The new combustion retardant can also be used for producing low fire risk synthetic rubbers.

The invention is further illustrated by examples of its implementation. In these examples:

the oxygen index, OI, is the minimum content of oxygen in a mixture with nitrogen at which stable combustion of a specimen is maintained after the removal of the source of ignition;

residual combustion time is the combustion time of the specimen after the removal of the source of ignition;

fire resistance class PV is a grading from 0 to 4, which was determined in accordance with GOST 28157-89, a state standard of the former USSR.

EXAMPLES OF THE IMPLEMENTATION OF THE INVENTION

Example 1

Production of the complex compound. 300 ml of chloroform are saturated with gaseous ammonia at temperature 10° C. A solution of dichloroanhydride of methylphosphonic acid in chloroform (60 g of dichloroanhydride of methylphosphonic acid dissolved in 200 ml of chloroform) is slowly added, over a period of two hours, to the solution obtained. Ammonia is continuously bubbled through the reaction mixture to maintain the alkaline medium (pH=9). The temperature of the process should not exceed 20° C. The sediment which forms is filtered off on a Bilchner fiunel and dried in a vacuum cupboard. The output of the synthesised product is 78.9%. The gross formula is $CH_{16.3}PN_{3.8}O_2Cl_{1.8}$.

Elemental analysis, found: C 5.8, H 8.1, P 14.3, N 24.9, Cl 30.7; calculated: C 5.8, H 7.8, P 14.9, N 25.5, Cl 30.6.

The formation of the complex compound was proved by the methods of thermogravimetric analysis (TGA), differential-scanning calorimetry (DSC) and X-ray photo-electronic spectroscopy (RPES).

The TGA curve of the complex compound of the ammonia salt of the amide of metaphosphonic acid and ammonium chloride includes one thermo-oxidising decomposition peak in the temperature interval 240–400° C. with a maximum at temperature 348° C., which is characteristic of the individual compound. The DSC data: show that the synthesised product melts at 202° C. (one peak), which is considerably higher than the melting point of the pure ammonia salt of the amide of methylphosphonic acid (124° C.).

The RPES spectrum of the synthesised product shows unusually low bond energy of the 2p electrons of the chlorine level (198.1 eV), which indicates the formation of the complex compound. The $N1_s$ spectrum includes two main peaks —at bond energy 400.2 eV, corresponding to the P—N bonds, and at bond energy 401.7 eV, corresponding to nitrogen in the form of ammonia, which is considerably lower than the nitrogen bond in $NH_4Cl$.

Example 2

A composition including 75 g of polypropylene crumbs and 25 g of CR in accordance with this invention is fed into a screw extruder. Moulding takes place at 170° C. The homogeneous melt enters a water bath (18–25° C.) and goes for granulation. The modified polyethylene has OI 27.6%, no residual combustion time, fire resistance class PV-0 in accordance with the USSR state standard (GOST 28157-89).

Example 3

A composition including 75 g of polypropylene crumbs and 25 g of CR in accordance with this invention encapsulated in a polyethylene shell (shell contains 10 wt. % CR, size of microcapsules 25 μm) is processed in accordance with Example 1. Moulding temperature—230° C. The modified polypropylene has OI 28.2%, no residual combustion time, fire resistance class PV-0.

Example 4

A composition including 90 g polyester crumbs and 10 g CR in accordance with this invention microencapsulated in a shell (shell contains 5 wt. % CR, microcapsule size 10 μm), is processed in accordance with Example 1. Moulding temperature —270° C. The modified polyester has OI 29.6%, no residual combustion time, fire resistance class —PV-0.

Example 5

A composition including 85 g polyester crumbs and 15 g CR in accordance with this invention microencapsulated in an ethylane shell (shell contains 2 wt. % CR, microcapsule size 10 em), is processed in accordance with Example 1. Moulding temperature —270° C. The modified polyester has IO 31.0%, no residual combustion time, fire resistance class —PV-0.

Example 6

100 g of epoxy resin are mixed with 10 g hardener and 15 g CR in accordance with this invention and allowed to set at room temperature for 48 hours; the solid composition modified in this way becomes a low combustibility material. OI (oxygen index) is 35, no residual combustion time, fire resistance class PV-0.

Example 7

Glass fibre is saturated with an epoxy composition produced in accordance with Example 5 and allowed to set at temperature 60–80° C. for 20–30 minutes. The composition obtained contains 40 wt. % binder (epoxy composition) and 60 wt. % filler (glass fibre). The composition material is of low combustibility, no residual combustion time, fire resistance class PV-0.

Example 8

A composition consisting of 60 g unsaturated polyester resin, 15 g CR in accordance with this invention microencapsulated in a polyaminopropylethoxysiloxane shell (shell contains 5 wt. % CR, microcapsule size 15 μm) and 25 g of staple fibre (viscose, polycaproamide) was pressed at temperature 180° C. and pressure 80 kg/cm². The plastics produced have OI 29.5%, no residual combustion time.

Example 9

A composition consisting of 80 g rubber mixture including butadiene styrene rubber and 20 g CR in accordance with this invention is thoroughly mixed, rolled at temperature 140–150° C. and the articles are then pressed at temperature 170–180° C. The modified rubber mixture has OI 28%, no residual combustion time.

Example 10

A composition consisting of 85 g rubber mixture based on isoprene rubber and 15 g CR in accordance with this invention microencapsulated in a polyaminopropylethoxysiloxane shell (shell contains 5 wt. % CR, microcapsule size 15 μm) is processed in accordance with Example 5. The modified rubber composition has OI 28.1%, no residual combustion time.

Example 11

A composition consisting of 80 g polymethyl methacrylate and 20 g CR in accordance with this invention is processed in accordance with Example 1 at temperature 220° C. The modified polymethyl methacrylate has OI 27.2%, no residual combustion time.

Example 12

A composition consisting of 75 g polycaproamide (PCA) and 25 g CR in accordance with this invention microencapsulated in an ethylane shell (shell contains 10 wt. % CR, microcapsule size 25 μm) is processed in accordance with Example 1. Moulding temperature 230° C. The modified PCA has OI 29%, no residual combustion time, fire resistance class PV-0.

Example 13 (comparative)

A composition including 85 g polyester crumbs and 15 g technical mixture consisting of 7.7 g ammonia salt of amide of methylphosphonic acid and 7.3 g ammonium chloride is processed in accordance with Example 4. The modified polyester has OI 27.6%.

Example 14 (comparative)

A composition including 75 g polypropylene crumbs and 25 g of a technical mixture including 12.8 g ammonia salt of amide of methylphosphonic acid and 12.2 g ammonium chloride is processed in accordance with Example 3. The modified polyester has OI 24.8%, fire resistance class PV-1.

Example 15 (comparative)

A composition including 75 g polyethylene crumbs and 25 g of a technical mixture including 12.8 g ammonia salt of amide of methylphosphonic acid and 12.2 g ammonium chloride is processed in accordance with Example 2. The modified polyester has OI 24.8%, fire resistance class PV-1.

Example 16 (comparative)

A composition including 75 g polycaproamide crumbs and 25 g of a technical mixture including 12.8 g ammonia salt of amide of methylphosphonic acid and 12.2 g ammonium chloride is processed in accordance with Example 12. The modified polyester has OI 24.8%, fire resistance class PV-1.

The comparative examples illustrate the fact that the proposed complex compound is a more effective antipyrene for polyethylene (Examples 2–15) polypropylene (Examples 3–14), polyester (Examples 5–13) and other polymers than a technical mixture of the two individual compounds of ammonia salt of diamide of methylphosphonic acid and ammonium chloride.

Furthermore, the diamide has low resistance to the action of hydrolising agents, and even under the effect of moisture in the air, diamide of methylphosphonic acid gradually passes through the ammonia salt into the methylphosphonic acid.

Therefore, the use of the proposed complex is a qualitatively new solution to the problem of reducing the combustibility of polymer materials.

What is claimed is:

1. Combustion retardant for polymer materials, consisting of a complex compound of ammonia salt of amide of alkylphosphonic acid with ammonium chloride of formula (I)

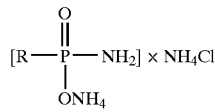

where R is the alkyl radical C-1-3.

2. Combustion retardant in accordance with claim 1, in which there are about 1.8 molecules of ammonium chloride to one molecule of ammonia salt of amide of alkylphosphonic acid.

3. Combustion retardant in accordance with claim 1, characterised in that it is microencapsulated in a polymer shell.

4. Combustion retardant in accordance with claim 3, characterised in that the said polymer shell is made of polyethylene.

5. Combustion retardant in accordance with claim 3, characterised in that the said polymer shell is made of polyorganosiloxanes.

6. Combustion retardant in accordance with claim 5, characterised in that the polyorganosiloxanes are selected from a group including polyvinylmethyldiethoxysiloxane and polyaminopropylethoxysiloxane.

7. Complex compound of ammonia salt of amide of alkylphosphonic acid with ammonium chloride of formula (I)

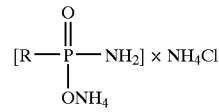

where R is the alkyl radical C-1-3.

8. Complex compound in accordance with claim 7, in which there are about 1.8 molecules of ammonium chloride to one molecule of ammonia salt of amide of alkylphosphonic acid.

9. Process for producing a complex compound of ammonia salt of amide of alkylphosphonic acid with ammonium chloride of formula (I)

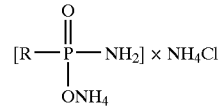

where R is the alkyl radical C-1-3:
consisting of the interaction of dichloroanhydride of alkylphosphonic acid with gaseous ammonia in a medium of organic solvent at temperature 10–200° C.

10. Process for producing low fire risk polymer materials by the introduction of the combustion retardant into the polymer in the course of its processing, characterised in that the combustion retardant used is a complex compound of ammonia salt of amide of alkylphosphonic acid with ammonium chloride of Formula (I)

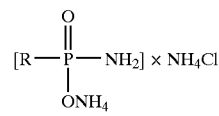

where R is the alkyl radical C-1-3.

11. Process for producing low fire risk polymer materials in accordance with claim 10, characterised in that it includes the following sequence of operations:
joint extrusion of the said combustion retardant with the polymer;
moulding the polymer fibre;
granulation.

12. Process for producing low fire risk polymer materials in accordance with claim 10, characterised in that it includes the following sequence of operations:
mixing of the said combustion retardant with the polymer composition;
rolling the mass;
pressing the articles.

13. Process in accordance with claim 10, characterised in that the combustion retardant is first microencapsulated in a polymer shell.

14. Process in accordance with claim 13, characterised in that the size of the microcapsules is 5–25 μm.

15. Process in accordance with claim 13, characterised in that the polymer shell is made of polyethylene with shell content including 10–15 wt. % of combustion retardant.

16. Process in accordance with claim 13, characterised in that polyorganosiloxanes are used for the polymer shell.

17. Process in accordance with claim 16, characterised in that the polyorganosiloxane consists of polymethyldiethoxysiloxanes with shell containing 2–5 wt. % of combustion retardant.

18. Process in accordance with claim 16, characterised in that the polyorganosiloxane used is polyaminopropylethoxysiloxane, with shell containing 2–5 wt. % of combustion retardant.

19. Process in accordance with claim 10, characterised in that polyethylene, polypropylene and copolymers of various compositions based on them are processed.

20. Process in accordance with claim 10, characterised in that polystyrene and copolymers of various compositions based on it are processed.

21. Low fire risk polyethylene produced by a process in accordance with claim 10.

22. Low fire risk polypropylene produced by a process in accordance with claim 10.

23. Low fire risk polystyrene produced by a process in accordance with claim 10.

24. Low fire risk copolymers based on polyethylene, polypropylene and polystyrene, produced by a process in accordance with claim 10.

25. Low fire risk polycaproamide materials produced by a process in accordance with claim 13.

26. Low fire risk polymethyl methacrylate compositions produced by a process in accordance with claim 11.

27. Process for producing low fire risk polymer materials by the introduction of combustion retardant into the polymer, characterised in that the combustion retardant used is a complex compound of ammonia salt of amide of alkylphosphonic acid with ammonium chloride of Formula (I)

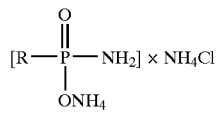

where R is the alkyl radical C-1–3 which is introduced into the polymer composition before it sets.

28. Process in accordance with claim 27, characterised in that polyesters are processed.

29. Process in accordance with claim 27, characterised in that epoxy resins are processed.

30. Low fire risk polyesters produced by a process in accordance with claim 27.

31. Low fire risk epoxy resins produced by a process in accordance with claim 27.

32. Process in accordance with claim 27, characterised in that a filler is introduced into the polymer composition along with the said combustion retardant, and as a result of the saturation of the filler with the setting polymer composition, low fire risk materials are produced.

33. Low fire risk composition materials produced by a process in accordance with claim 32.

34. Process for producing low fire risk polymer materials, characterised in that a complex compound of ammonia salt of amide of alkylphosphonic acid with ammonium chloride of Formula (I)

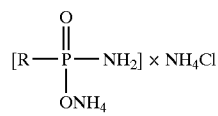

where R is the alkyl radical C-1–3 is introduced into a polymer composition including synthetic rubber, after which it is rolled before the article is pressed.

35. Low fire risk synthetic rubbers produced by a process in accordance with claim 34.

* * * * *